US010109171B1

(12) United States Patent
M A M et al.

(10) Patent No.: US 10,109,171 B1
(45) Date of Patent: Oct. 23, 2018

(54) SYSTEMS AND METHODS FOR PERFORMING SECURITY ACTIONS BASED ON PEOPLE'S ACTUAL REACTIONS TO INTERACTIONS

(71) Applicant: Symantec Corporation, Mountain View, CA (US)

(72) Inventors: Arun Karthick M A M, Chennai (IN); Ramakrishnan Meenakshi Sundaram, Tamilnadu (IN); Bruce McCorkendale, Manhattan Beach, CA (US)

(73) Assignee: Symantec Corporation, Mountain View, CA (US)

( * ) Notice: Subject to any disclaimer, the term of this patent is extended or adjusted under 35 U.S.C. 154(b) by 0 days.

(21) Appl. No.: 15/627,480

(22) Filed: Jun. 20, 2017

(51) Int. Cl.
| | |
|---|---|
| *G08B 23/00* | (2006.01) |
| *G08B 21/02* | (2006.01) |
| *A61B 5/0205* | (2006.01) |
| *A61B 5/16* | (2006.01) |
| *A61B 5/021* | (2006.01) |
| *A61B 5/024* | (2006.01) |

(52) U.S. Cl.
CPC .......... *G08B 21/02* (2013.01); *A61B 5/02055* (2013.01); *A61B 5/165* (2013.01); *A61B 5/021* (2013.01); *A61B 5/024* (2013.01)

(58) Field of Classification Search
CPC ..... G08B 21/02; A61B 5/02055; A61B 5/165; A61B 5/021; A61B 5/024
See application file for complete search history.

(56) References Cited

U.S. PATENT DOCUMENTS

| | | | |
|---|---|---|---|
| 8,925,037 B2 | 12/2014 | Marino et al. | |
| 2014/0324749 A1* | 10/2014 | Peters | G09B 7/04 706/46 |
| 2015/0249584 A1* | 9/2015 | Cherifi | H04L 43/065 709/224 |
| 2017/0132215 A1* | 5/2017 | Baughman | G06F 17/2818 |
| 2017/0318261 A1* | 11/2017 | Dalvi | G06T 19/006 |

OTHER PUBLICATIONS

Doerrfeld; http://nordicapis.com/20-emotion-recognition-apis-that-will-leave-you-impressed-and-concerned/; Dec. 31, 2015.
http://www.awakelabs.com/; As accessed on Jun. 16, 2017.
(Continued)

*Primary Examiner* — Brian Zimmerman
*Assistant Examiner* — Kevin Lau
(74) *Attorney, Agent, or Firm* — FisherBroyles, LLP

(57) ABSTRACT

The disclosed computer-implemented method for performing security actions based on people's actual reactions to interactions may include (i) detecting an interaction (e.g., an interaction with a digital communication) of a monitored person (e.g., a child), (ii) estimating the monitored person's expected reaction to the interaction, (iii) using contemporaneous sensor data to estimate the monitored person's actual reaction to the interaction, and (iv) performing a security action based at least in part on a comparison of the monitored person's expected reaction and the monitored person's actual reaction. Various other methods, systems, and computer-readable media are also disclosed.

20 Claims, 8 Drawing Sheets

(56) References Cited

OTHER PUBLICATIONS

Wikipedia; Microexpression; https://en.wikipedia.org/wiki/Microexpression; As accessed on Jun. 16, 2017.
Chen; EMC: Emotion-Aware Mobile Cloud Computing in 5g; http://ieeexplore.ieee.org/stamp/stamp.jsp?arnumber=7064900; Mar. 24, 2015.
Chowdhury; MediAlly; A provenance-aware remote health monitoring middleware; http://ieeexplore.ieee.org/stamp/stamp.jsp?arnumber=5466985; May 20, 2010.
Ayzenberg et al.; FEEL; Frequent EDA and Event Logging—A mobile social interaction stress monitoring system; http://dl.acm.org/citation.cfm?id=2223802; May 5, 2012.
Thompson; Systems and Methods for Eliciting Emotional Threat Responses from Computing Users; U.S. Appl. No. 15/459,424, filed Mar. 15, 2017.
Sokolov et al.; Systems and Methods for Analyzing Emotional Responses to Online Interactions; U.S. Appl. No. 15/181,457, filed Jun. 14, 2016.

\* cited by examiner

SYSTEMS AND METHODS FOR PERFORMING SECURITY ACTIONS BASED ON PEOPLE'S ACTUAL REACTIONS TO INTERACTIONS

BACKGROUND

Today, children are digitally interacting with more and more information and people. With a typical child's increased number of online interactions, there may be more opportunities for the typical child to be exposed to cyberbullying and inappropriate topics such as addictive substances. For these and other reasons, parental-control, child-safety, and other cybersecurity features are likely to become increasingly important to parents and guardians as a way to protect children from harmful information and people.

Parental-control features of today's typical parental-control software may use various forms of content filtering to prevent a child from accessing categories of content that have been deemed generally inappropriate for the child based on such things as the age of the child, recommendations from online child-safety advocates, family norms, and/or societal norms. Unfortunately, existing classification techniques used by today's parental-control software to classify a particular item of content as belonging to an inappropriate category are prone to error and often have high levels of false-positive and false-negative classifications.

Child-safety features of today's typical parental-control software may detect cyberbullying through sentiment analysis and/or topic mining of the text of the communications being read by a child. Unfortunately, existing sentiment-analysis and topic-mining techniques used by today's parental-control software to detect cyberbullying often used generalized models that may perform poorly when applied to specific instances of cyberbullying since the way that a child is bullied is generally specific to the child's unique attributes, environment, and experiences. The instant disclosure, therefore, identifies and addresses a need for systems and methods for performing security actions based on people's, especially children's, actual reactions to their interactions with digital content, digital communications, people, and their environments.

SUMMARY

As will be described in greater detail below, the instant disclosure describes various systems and methods for performing security actions based on people's actual reactions to interactions. In one example, a method for performing security actions based on people's actual reactions to interactions may include (i) detecting an interaction of a monitored person, (ii) estimating the monitored person's expected reaction to the interaction, (iii) using contemporaneous sensor data to estimate the monitored person's actual reaction to the interaction, and (iv) performing a security action based at least in part on a comparison of the monitored person's expected reaction and the monitored person's actual reaction.

In one embodiment, the monitored person may be a child, and performing the security action may include reporting the interaction to the child's guardian. In some embodiments, the step of detecting the interaction of the monitored person may include detecting a communication that the monitored person views, the step of estimating the monitored person's expected reaction to the interaction may include determining that the monitored person's expected reaction to the communication should be positive, the step of using the contemporaneous sensor data to estimate the monitored person's actual reaction to the interaction may include using the contemporaneous sensor data to determine that the monitored person's actual reaction to the communication was negative, and the step of performing the security action may include determining, based at least in part on the difference between the monitored person's expected reaction to the communication and the monitored person's actual reaction to the communication, that the communication is a form of cyberbullying.

In one embodiment, the step of estimating the monitored person's expected reaction to the interaction may include (i) using additional sensor data to estimate at least one additional monitored person's actual reaction to a similar interaction and (ii) using the at least one additional monitored person's actual reaction to the similar interaction to establish a baseline normal reaction to the interaction. In such embodiments, the monitored person's expected reaction to the interaction may be based at least in part on the baseline normal reaction to the interaction. In some examples, performing the security action may include determining, based at least in part on a difference between the monitored person's actual reaction and the baseline normal reaction, that the monitored person's actual reaction to the interaction is abnormal.

In some embodiments, the step of estimating the monitored person's expected reaction to the interaction may include using past sensor data to estimate a prior reaction of the monitored person to a similar interaction, and the monitored person's expected reaction to the interaction may be based at least in part on the prior reaction of the monitored person to the similar interaction. In some examples, the step of performing the security action may include determining, based at least in part on a difference between the monitored person's actual reaction and the prior reaction of the monitored person to the similar interaction, that the monitored person's actual reaction to the interaction is abnormal.

In some examples, the step of using the contemporaneous sensor data to estimate the monitored person's actual reaction to the interaction may include (i) using contemporaneous camera data to detect a microexpression that was exhibited by the monitored person as the monitored person had the interaction and (ii) deriving the monitored person's actual reaction to the interaction based at least in part on the microexpression that was exhibited by the monitored person. In one embodiment, the contemporaneous sensor data may indicate an actual physical reaction of the monitored person to the interaction, and the step of using the contemporaneous sensor data to estimate the monitored person's actual reaction to the interaction may include estimating the monitored person's actual emotional reaction to the interaction based at least in part on the actual physical reaction of the monitored person to the interaction. In some embodiments, the contemporaneous sensor data may indicate (i) the monitored person's heartrate at the time of the interaction, (ii) the monitored person's blood pressure at the time of the interaction, (iii) the monitored person's stress level at the time of the interaction, and/or (iv) the monitored person's skin temperature at the time of the interaction.

In one embodiment, the step of detecting the interaction of the monitored person may include detecting digital content with which the monitored person interacts, the step of estimating the monitored person's expected reaction to the interaction may include estimating the monitored person's expected reaction to the digital content, and the step of using the contemporaneous sensor data to estimate the monitored person's actual reaction to the interaction may include using the contemporaneous sensor data to estimate the monitored person's actual reaction to the digital content.

In some embodiments, the step of detecting the interaction of the monitored person may include detecting an additional person with which the monitored person interacts, the step of estimating the monitored person's expected reaction to the interaction may include estimating the monitored person's expected reaction to the additional person, and the step of using the contemporaneous sensor data to estimate the monitored person's actual reaction to the interaction may include using the contemporaneous sensor data to estimate the monitored person's actual reaction to the additional person. In other embodiments, the step of detecting the interaction of the monitored person may include detecting an environment with which the monitored person interacts, the step of estimating the monitored person's expected reaction to the interaction may include estimating the monitored person's expected reaction to the environment, and the step of using the contemporaneous sensor data to estimate the monitored person's actual reaction to the interaction may include using the contemporaneous sensor data to estimate the monitored person's actual reaction to the environment. In at least one embodiment, the step of estimating the monitored person's expected reaction to the interaction may include estimating the monitored person's expected emotional reaction to the interaction, and the step of using the contemporaneous sensor data to estimate the monitored person's actual reaction to the interaction may include using the contemporaneous sensor data to estimate the monitored person's actual emotional reaction to the interaction.

In one embodiment, a system for performing security actions based on people's actual reactions to interactions may include several modules stored in memory, including (i) a detecting module that detects an interaction of a monitored person, (ii) an estimating module that estimates the monitored person's expected reaction to the interaction, (iii) a sensing module that uses contemporaneous sensor data to estimate the monitored person's actual reaction to the interaction, and (iv) a security module that performs a security action based at least in part on a comparison of the monitored person's expected reaction and the monitored person's actual reaction. The system may also include at least one physical processor that executes the detecting module, the estimating module, the sensing module, and the security module.

In some examples, the above-described method may be encoded as computer-readable instructions on a non-transitory computer-readable medium. For example, a computer-readable medium may include one or more computer-executable instructions that, when executed by at least one processor of a computing device, may cause the computing device to (i) detect an interaction of a monitored person, (ii) estimate the monitored person's expected reaction to the interaction, (iii) use contemporaneous sensor data to estimate the monitored person's actual reaction to the interaction, and (iv) perform a security action based at least in part on a comparison of the monitored person's expected reaction and the monitored person's actual reaction.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of example embodiments and are a part of the specification. Together with the following description, these drawings demonstrate and explain various principles of the instant disclosure.

Figure 1:
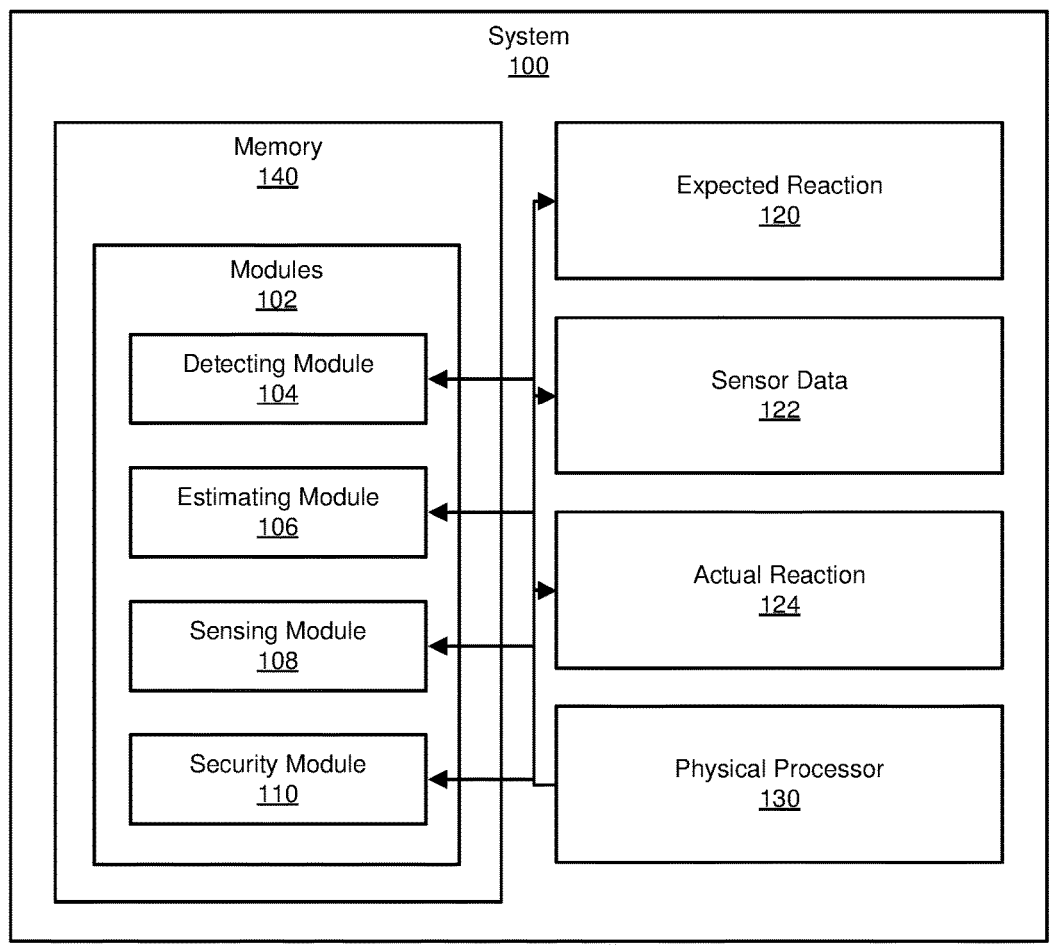
FIG. 1 is a block diagram of an example system for performing security actions based on people's actual reactions to interactions.

Throughout the drawings, identical reference characters and descriptions indicate similar, but not necessarily identical, elements. While the example embodiments described herein are susceptible to various modifications and alternative forms, specific embodiments have been shown byway of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

The present disclosure is generally directed to systems and methods for performing security actions based on people's actual reactions to interactions. As will be explained in greater detail below, by monitoring a child's contemporaneous physical and emotional reactions to any communications, media, people, and environments with which the child interacts, the systems and methods described herein may personalize various parental-control, child-safety, and/or cybersecurity actions and features to the child. For example, by monitoring a child's contemporaneous physical and emotional reactions to the digital communications that the child views and/or the people with which the child interacts, these systems and methods may determine, in a way that is individualized to the child, when such communications may be forms of cyberbullying and/or when such people may be bullying or otherwise harming the child. Additionally, by monitoring a child's contemporaneous physical and emotional reactions to the digital content that the child views, these systems and methods may determine when the child reacts in an abnormal way to certain types of digital content (e.g., with inappropriate excitement, interest, or obsession) and may perform suitable actions in response to this determination (e.g., preventing or limiting the child's access to these types of digital content).

In addition, the systems and methods described herein may improve the functioning of a computing device by improving the level of safety at which children may interact with digital content using the computing device. These systems and methods may also improve the fields of parental-control, child-safety, and/or cybersecurity by tailoring parental-control, child-safety, and/or cybersecurity actions and features for specific children and situations. Embodiments of the instant disclosure may also provide various other advantages and features, as discussed in greater detail below.

Figure 2:
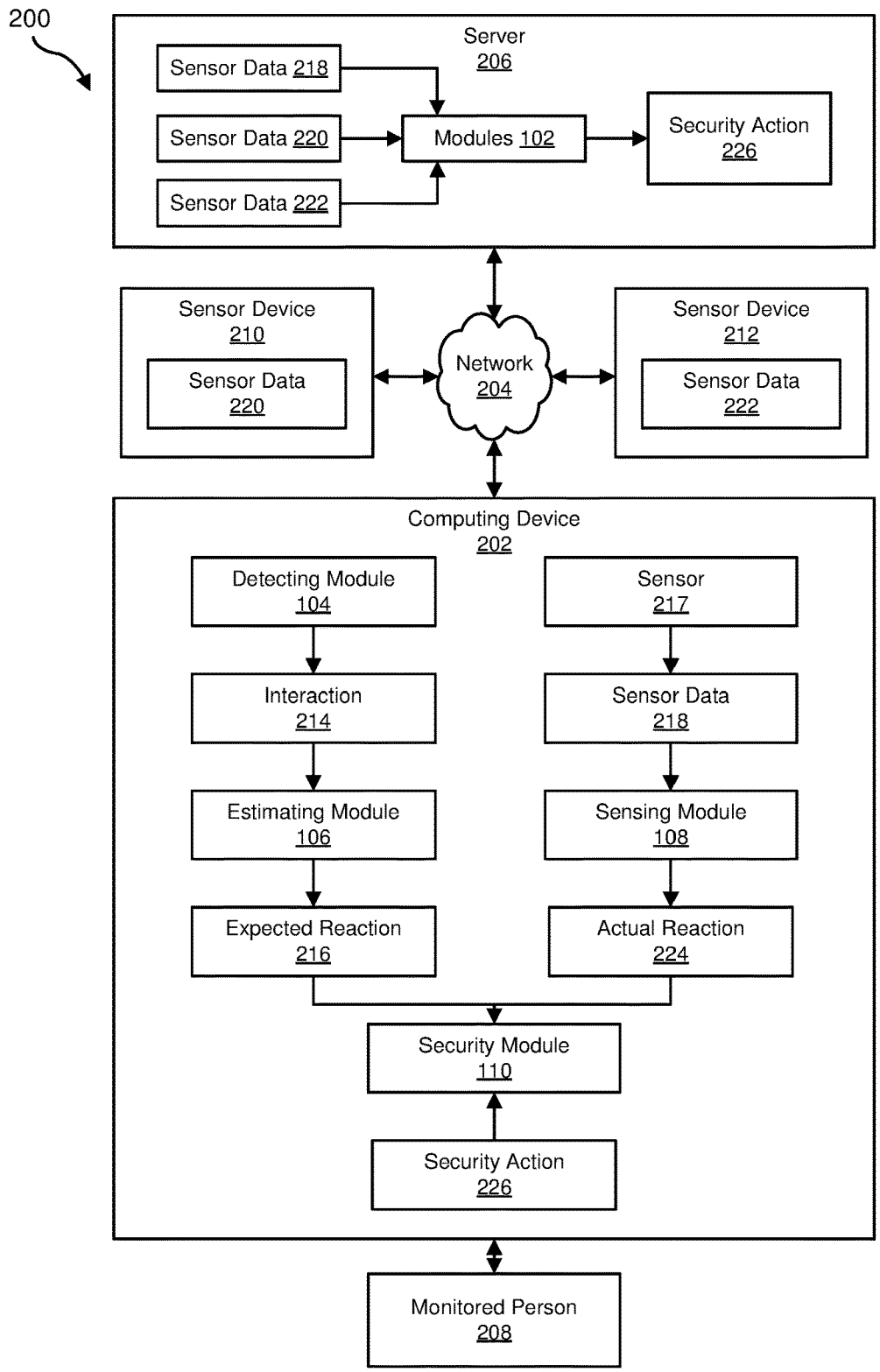
FIG. 2 is a block diagram of an additional example system for performing security actions based on people's actual reactions to interactions.

The following will provide, with reference to FIGS. 1-2, detailed descriptions of example systems for performing security actions based on people's actual reactions to interactions. Detailed descriptions of corresponding computer-implemented methods will also be provided in connection with FIG. 3. Detailed descriptions of example data flows will be provided in connection with FIGS. 4-6. In addition, detailed descriptions of an example computing system and network architecture capable of implementing one or more of the embodiments described herein will be provided in connection with FIGS. 7 and 8, respectively.

FIG. 1 is a block diagram of an example system 100 for performing security actions based on people's actual reactions to interactions. As illustrated in this figure, example system 100 may include one or more modules 102 for performing one or more tasks. As will be explained in greater detail below, modules 102 may include a detecting module 104, and estimating module 106, a sensing module 108, and a security module 110. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, and as will be described in greater detail below, one or more of modules 102 may represent modules stored and configured to run on one or more computing devices, such as the devices illustrated in FIG. 2 (e.g., computing device 202 and/or server 206). One or more of modules 102 in FIG. 1 may also represent all or portions of one or more special-purpose computers configured to perform one or more tasks.

As illustrated in FIG. 1, example system 100 may also include one or more memory devices, such as memory 140. Memory 140 generally represents any type or form of volatile or non-volatile storage device or medium capable of storing data and/or computer-readable instructions. In one example, memory 140 may store, load, and/or maintain one or more of modules 102. Examples of memory 140 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 1, example system 100 may also include one or more physical processors, such as physical processor 130. Physical processor 130 generally represents any type or form of hardware-implemented processing unit capable of interpreting and/or executing computer-readable instructions. In one example, physical processor 130 may access and/or modify one or more of modules 102 stored in memory 140. Additionally or alternatively, physical processor 130 may execute one or more of modules 102 to facilitate performing security actions based on people's actual reactions to interactions. Examples of physical processor 130 include, without limitation, microprocessors, microcontrollers, Central Processing Units (CPUs), Field-Programmable Gate Arrays (FPGAs) that implement soft-core processors, Application-Specific Integrated Circuits (ASICs), portions of one or more of the same, variations or combinations of one or more of the same, and/or any other suitable physical processor.

As illustrated in FIG. 1, example system 100 may also include one or more additional elements, such as an expected reaction 120, sensor data 122, and an actual reaction 124. Expected reaction 120 generally represents any type or form of information that identifies or indicates an expected reaction of a person to an interaction. Sensor data 122 generally represents any type or form of data that has been acquired from a sensor (e.g., a camera or a health sensor) and that may contain information from which an actual reaction of a person to an interaction may be deduced. Actual reaction 124 generally represents any type or form of information that identifies or indicates an actual reaction of a person to an interaction.

Example system 100 in FIG. 1 may be implemented in a variety of ways. For example, all or a portion of example system 100 may represent portions of example system 200 in FIG. 2. As shown in FIG. 2, system 200 may include a computing device 202 in communication with a server 206 via a network 204. In one example, all or a portion of the functionality of modules 102 may be performed by computing device 202, server 206, and/or any other suitable computing system. As will be described in greater detail below, one or more of modules 102 from FIG. 1 may, when executed by at least one processor of computing device 202 and/or server 206, enable computing device 202 and/or server 206 to make security determinations based on people's reactions to monitored interactions. For example, and as will be described in greater detail below, one or more of modules 102 may cause computing device 202 and/or server 206 to detect an interaction 214 of monitored person 208, (ii) estimate an expected reaction 216 of monitored person 208 to interaction 214, (iii) use contemporaneous sensor data 218, contemporaneous sensor data 220, and/or contemporaneous sensor data 222 to estimate an actual reaction 224 of monitored person 208 to interaction 214, and (iv) perform a security action 226 based at least in part on a comparison of expected reaction 216 and actual reaction 224.

Computing device 202 generally represents any type or form of computing device capable of reading computer-executable instructions. In one example, computing device 202 may represent a personal computing device of a monitored person on which monitoring software has been installed. In another example, computing device 202 may represent a testing device that a monitored person is instructed to use so that the monitored person's reactions to various interactions and stimuli may be monitored. Additional examples of computing device 202 include, without limitation, laptops, tablets, desktops, servers, cellular phones, Personal Digital Assistants (PDAs), multimedia players, embedded systems, wearable devices (e.g., smart watches, smart glasses, etc.), health monitoring devices, gaming consoles, variations or combinations of one or more of the same, and/or any other suitable computing device.

As shown in FIG. 2, computing device 202 may include a sensor 217. Sensor 217 generally represents any type or form of sensor that is capable of detecting or measuring (i) an attribute of a person that may indicate the person's reaction to something with which they are interacting and/or (ii) an attribute of the thing to which the person is reacting. Examples of sensor 217 include, without limitation, global positioning system (GPS) sensors, network sensors (e.g., a BLUETOOTH adapter), audio sensors (e.g., a microphone), image sensors, accelerometers, gyroscopes, light sensors, proximity sensors, temperature sensors, barometers, pedometers, and/or any other sensor capable of gathering information about monitored person 208 and/or the environments within which computing device 202 operates.

Server 206 generally represents any type or form of computing device that is capable of reading computer-executable instructions. In one example, server 206 may represent a server-side computing device that performs some or all of the steps described herein. Additional examples of server 206 include, without limitation, security servers, application servers, web servers, storage servers, and/or database servers configured to run certain software applications and/or provide various security, web, storage, and/or database services. Although illustrated as a single entity in FIG. 2, server 206 may include and/or represent a plurality of servers that work and/or operate in conjunction with one another.

Sensor device 210 and sensor device 212 generally represent any type or form of computing device that includes one or more sensors, like sensor 217 described above, that are capable of detecting or measuring (i) an attribute of a monitored person that may indicate the monitored person's reaction to something with which they are interacting and/or (ii) an attribute of the thing to which the person is reacting. In some examples, computing device 202 may represent a primary computing device of a monitored person, and sensor device 210 and sensor device 212 may represent secondary computing devices that are capable of collecting contemporaneous sensor data about the monitored person, the monitored person's interactions, and/or the monitored person's environment. Examples of sensor device 210 and sensor device 212 include, without limitation, security cameras (e.g., home-based security cameras, school-based security cameras, etc.), other cameras that may capture information about a monitored user, audio recording devices, wearable devices of the monitored person (e.g., smart watches, smart glasses, fitness-monitoring devices, health-monitoring devices, etc.), and/or computing devices of the monitored person's guardians. While not shown in FIG. 2, sensor device 210 and/or sensor device 212 may include one or more of modules 102 and may perform one or more of the steps described herein.

Network 204 generally represents any medium or architecture capable of facilitating communication or data transfer. In one example, network 204 may facilitate communication between computing device 202 and server 206. In this example, network 204 may facilitate communication or data transfer using wireless and/or wired connections. Examples of network 204 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network.

Figure 3:
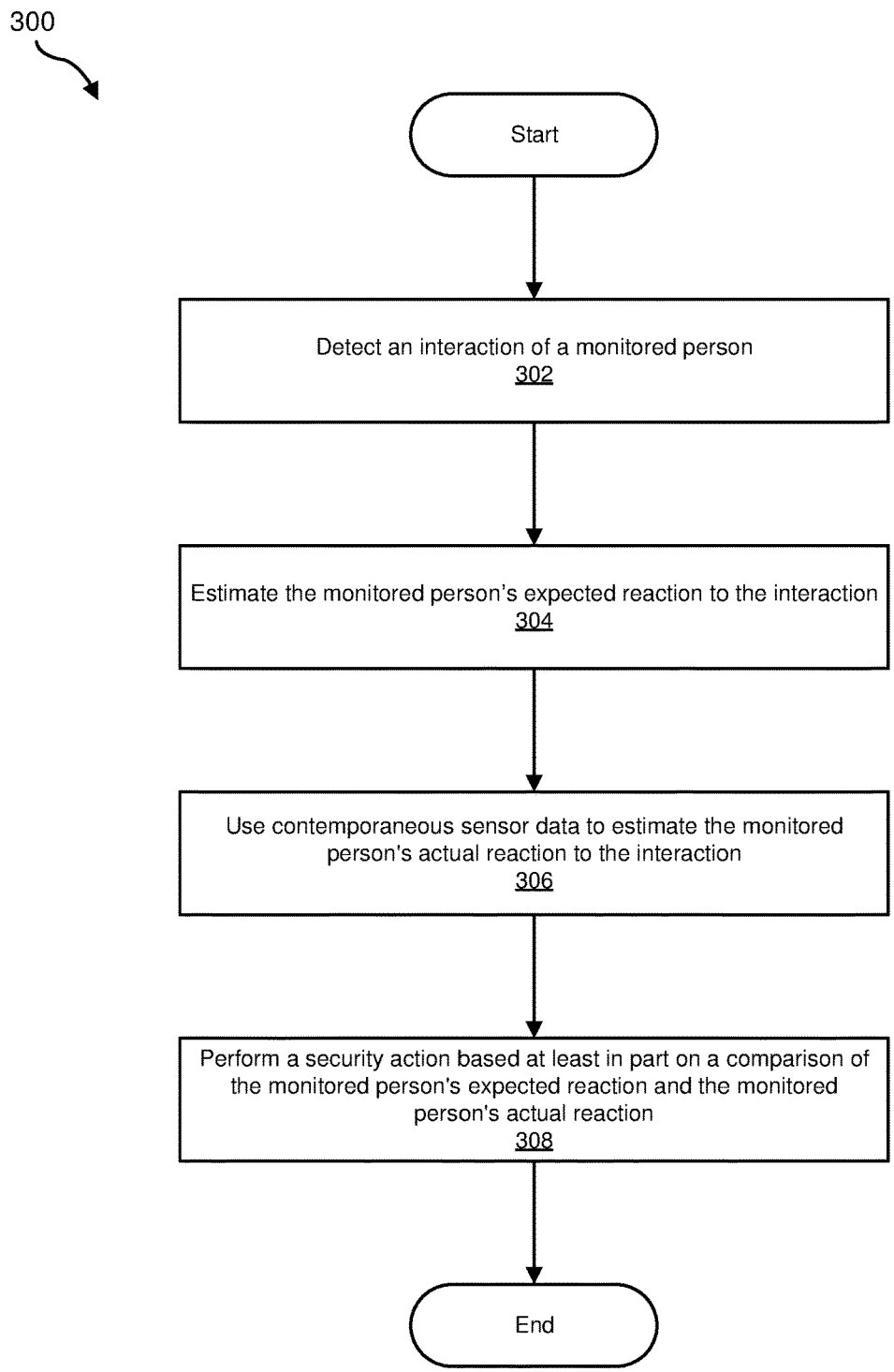
FIG. 3 is a flow diagram of an example method for performing security actions based on people's actual reactions to interactions.
Figure 4:
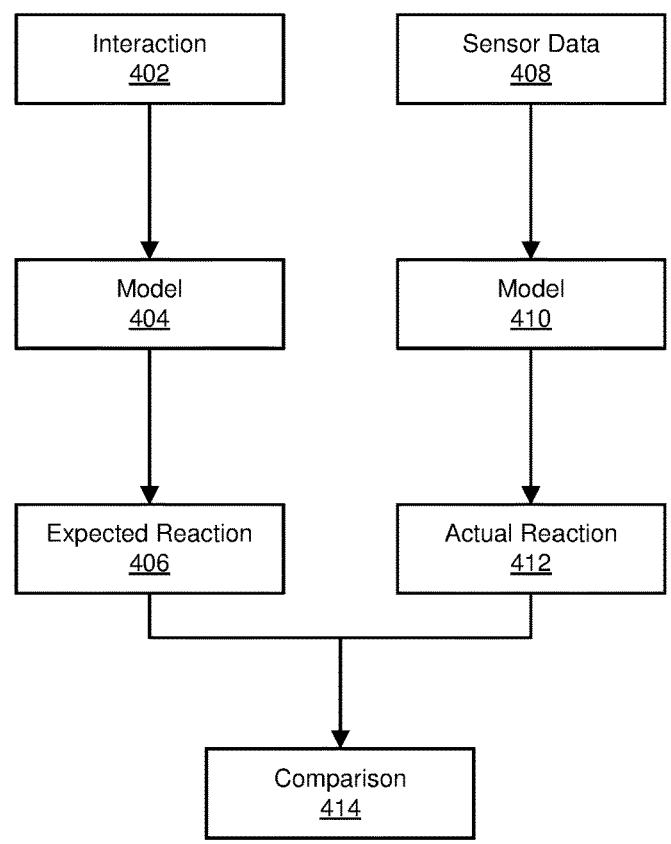
FIG. 4 is a flow diagram of an exemplary data flow for comparing an expected reaction to an interaction with an actual reaction to the interaction.

FIG. 3 is a flow diagram of an example computer-implemented method 300 for performing security actions based on people's actual reactions to interactions. The steps shown in FIG. 3 may be performed by any suitable computer-executable code and/or computing system, including system 100 in FIG. 1, system 200 in FIG. 2, and/or variations or combinations of one or more of the same. In one example, each of the steps shown in FIG. 3 may represent an algorithm whose structure includes and/or is represented by multiple sub-steps, examples of which will be provided in greater detail below.

As illustrated in FIG. 3, at step 302 one or more of the systems described herein may detect an interaction of a monitored person. For example, detecting module 104 may, as part of computing device 202 in FIG. 2, detect interaction 214 of monitored person 208.

The systems described herein may monitor the interactions of various types of people. In one example, detecting module 104 may monitor the interactions of a child on behalf of the child's guardian or parent. In other examples, detecting module 104 may monitor the interactions of a patient on behalf of the patient's therapist or physician, the interactions of an employee on behalf of an employer, and/or the interactions of any other person that has agree to be monitored.

The systems described herein may detect various kinds of interactions. In one example, detecting module 104 may detect, as part of a computing device, various types or forms of digital content with which a user of the computing device is interacting. Examples of digital content include, without limitation, digital communications (e.g., instant messages, emails, social media posts, telephone calls, video calls, and online interactions), videos, images, movies, songs, books, documents, applications, websites, webpages, and/or any other form of digital information.

In other examples, detecting module 104 may detect various attributes of a monitored person's environment with which the monitored person may interact and/or various attributes of the situations in which the monitored person is involved. For example, detecting module 104 may detect various attributes of the location of the monitored person (e.g., noise levels, crowdedness, type of location, coordinates of the location, etc.), various attributes of any people surrounding the monitored person (e.g., names, ages, genders, moods, etc.), various attributes of any animals surrounding the monitored person, various attributes of any media surrounding the monitored person, various attributes of any foods surrounding the monitored person, and/or various attributes of any other objects that may surround the monitored person. In one example, detecting module 104 may identify the people that surround a monitored person by detecting wireless signals (e.g., Bluetooth signals) of the people's computing devices.

The systems described herein may detect the interactions of a monitored person in a variety of ways. For example, detecting module 104 may detect the interactions of a monitored person as part of parental-control software that is installed on a computing device of the monitored person and that monitors and/or filters digital content that may be accessed by the monitored person via the computing device. In another example, detecting module 104 may detect the interactions of a monitored person as part of a security system that may include security cameras and/or other security sensors that may be used to detect an interaction of a monitored person. In other examples, detecting module 104 may detect the interactions of a monitored patient as part of an evaluation system that monitors the patient's reactions to interactions in order to determine whether the patient has various conditions such as autism.

At step 304, one or more of the systems described herein may estimate the monitored person's expected reaction to the interaction. For example, estimating module 106 may, as part of computing device 202 or server 206 in FIG. 2, estimate expected reaction 216 of the monitored person 208 to interaction 214.

The systems described herein may estimate various types of reactions of a monitored person to his or her interactions. For example, estimating module 106 may estimate a monitored person's physical reactions or responses (e.g., changes to the monitored person's body) to his or her interactions. Examples of such physical reactions include, without limitation, microexpressions, facial expressions, postures, tensed muscles, sweating, auditory expressions (e.g., crying, yelling, or laughing), dilated pupils, glassy eyes, slurred speech, physical signs of exhaustion, heartrate, blood pressure, stress level, weight changes, bruises, infections, and skin temperature. Additionally or alternatively, estimating module 106 may estimate a monitored person's emotional or mental reactions or responses (e.g., changes to the monitored person's mind) to his or her interactions. Examples of emotional reactions include, without limitation, happiness, fear, pride, horror, comfort, euphoria, suspicion, indecision, excitement, ecstasy, agitation, gladness, relaxation, gratitude, inattentiveness, love, shock, contentment, a fight-or-flight response, nervousness, interest, dread, being threatened, grief, desire, joy, remorse, acceptance, frustration, hate, homesickness, unhappiness, lust, confusion, constraint, anger, embarrassment, detachment, delight, loss, vulnerability, avoiding, outrage, pity, guilt, hope, apathy, wonder, appreciation, sorrow, kindness, distress, anticipation, amusement, unease, tolerance, repulsion, alertness, disappointment, suffering, rage, attentiveness, angst, depression, timidity, being insulted, rashness, shyness, stress, jealousy, envy, surprise, pleasure, reluctance, despair, confidence, self-pity, shame, sadness, bitterness, disgust, calmness, caution, loneliness, boredom, heightened awareness, exhaustion, discomfort, terror, displeasure, alarm, patience, indifference, discontentment, closeness, apprehension, pain, weariness, suspense, composure, being disturbed, and/or any other positive, negative, or neutral emotional response.

The systems described herein may estimate a monitored person's expected reaction to an interaction in any suitable manner. In general, estimating module 106 may use a suitable model (e.g., model 404 in FIG. 4) that takes as input information about a monitored person's interactions and outputs the monitored person's expected reaction to the interactions. In some examples, estimating module 106 may estimate a monitored person's expected reaction to an interaction using a suitable classification model. In some examples, estimating module 106 may use a classification model to classify the interaction of the monitored person as likely to cause a positive, negative, neutral, or unknown reaction. In other examples, estimating module 106 may estimate a monitored person's expected reaction to an interaction using sentiment analysis and/or topic modeling of the content or communications with which the monitored person interacts. In some examples, estimating module 106 may use sentiment analysis and/or topic modeling of the content or communications with which the monitored person interacts in order to predict whether the monitored person will have a positive, negative, neutral, or unknown reaction to the content or communications.

Additionally or alternatively, estimating module 106 may use past actual reactions to interactions to estimate or predict a monitored person's expected reactions to the same or similar interactions. In one example, estimating module 106 may use past actual reactions of other monitored people with the same or similar demographic characteristics of the monitored person to their interactions to estimate or predict the expected reactions of the monitored person to the same or similar interactions. For example, estimating module 106 may use other monitored people's past actual reactions to communications from a particular person to estimate or predict the expected reactions of the monitored person to a communication from the same person. In another example, estimating module 106 may use other monitored people's past actual reactions to digital content that involves a certain topic to estimate or predict the expected reactions of the monitored person to digital content that involves the same or similar topics. Similarly, estimating module 106 may use other monitored people's past actual reactions to various environments or environmental conditions to estimate or predict the expected reactions of the monitored person to the same or similar environments or environmental conditions.

Figure 5:
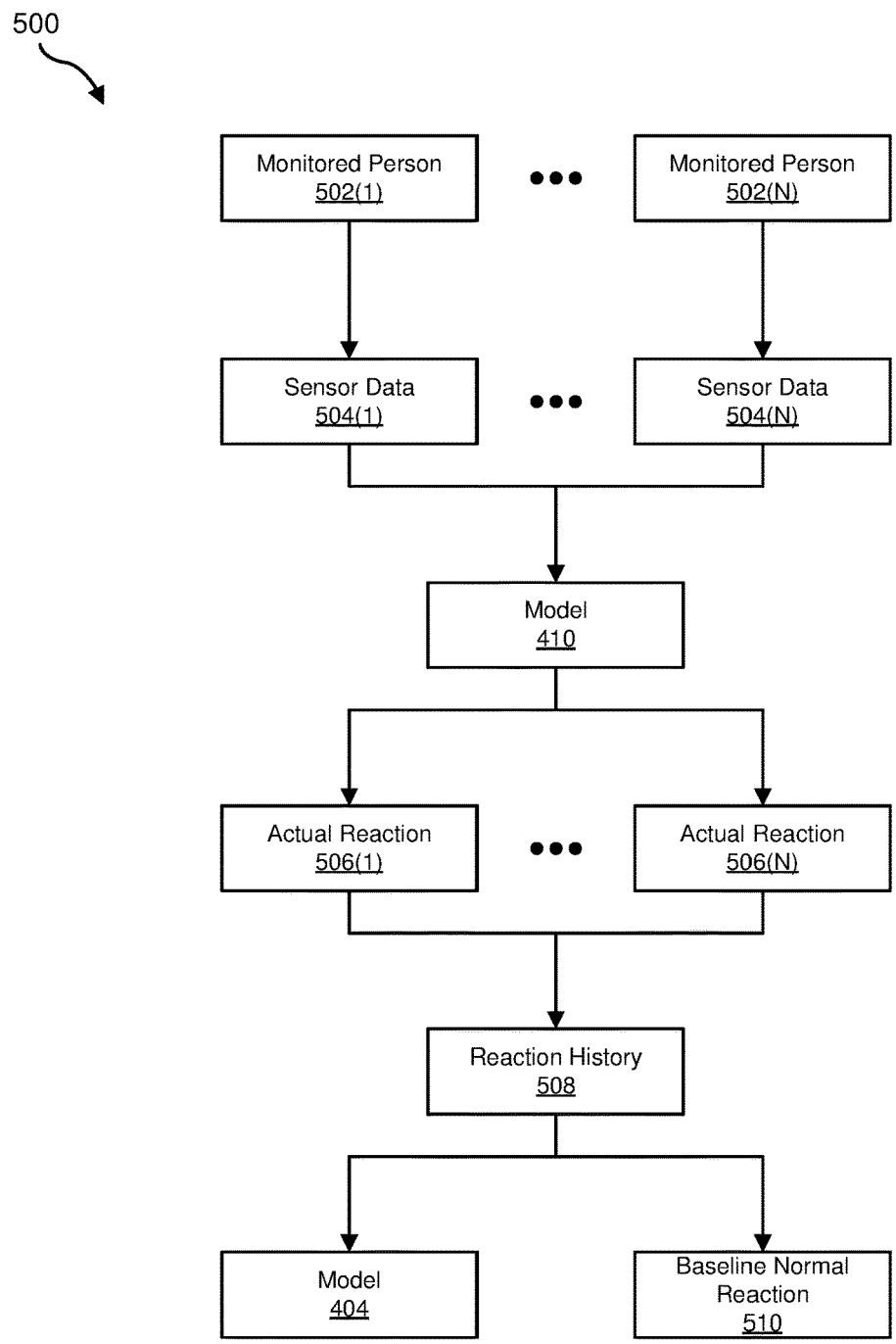
FIG. 5 is a flow diagram of an exemplary data flow for compiling and using histories of many people's actual reactions to interactions.

FIG. 5 illustrates an exemplary data flow by which the systems and methods described herein may compile a reaction history 508 that contains the actual reactions of monitored persons 502(1)-(N) to a particular type of interaction. In this example, the systems and methods described herein may apply model 410 to sensor data 504(1)-(N) to determine actual reactions 506(1)-(N) to the particular type of interaction of monitored persons 502(1)-(N), respectively. In some examples, the systems and methods described herein may use reaction history 508 to train a model 404 to estimate expected reactions to similar interactions. Additionally or alternatively, the systems and methods described herein may use reaction history 508 to derived a baseline normal reaction 510 to the same or similar interactions. In some examples, baseline normal reaction 510 may be used as or to determine an expected reaction of a monitored person (e.g., a monitored person that has the same or similar demographic characteristics of monitored persons 502(1)-(N)) to the same or similar interactions.

Additionally or alternatively, estimating module 106 may use a monitored person's past reactions to his or her interactions to estimate or predict his or her expected reactions to the same or similar interactions. For example, estimating module 106 may use a monitored person's prior actual reactions to communications from a particular person to estimate or predict the expected reactions of the monitored person to an additional communication from the same person. In another example, estimating module 106 may use a monitored person's prior actual reactions to digital content that involves a certain topic to estimate or predict the expected reactions of the monitored person to digital content that involves the same or similar topics. Similarly, estimating module 106 may use a monitored person's prior actual reactions to various environments or environmental conditions to estimate or predict the expected reactions of the monitored person to the same or similar environments or environmental conditions.

Figure 6:
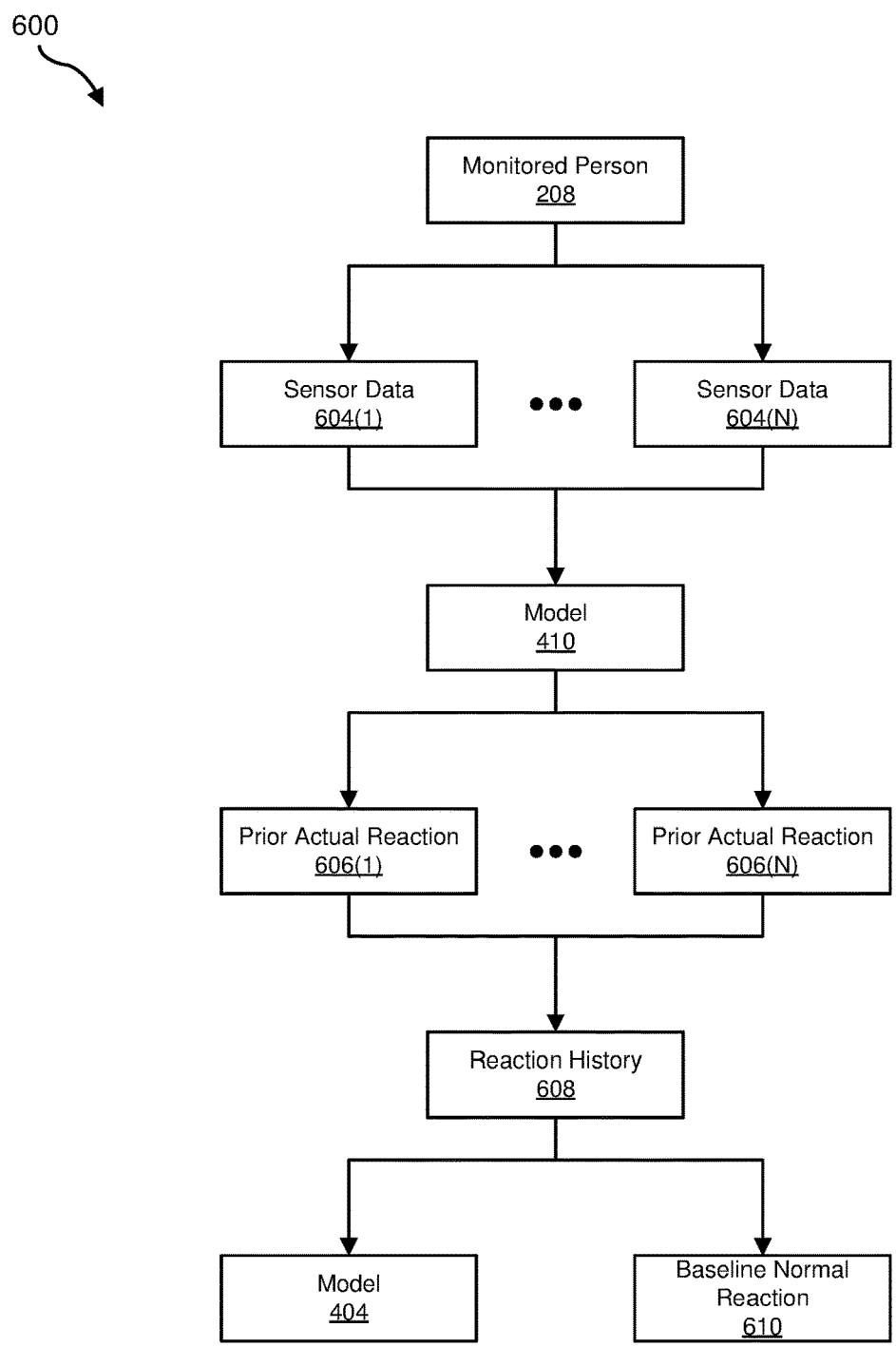
FIG. 6 is a flow diagram of an exemplary data flow for compiling and using histories of a single person's actual reactions to interactions.

FIG. 6 illustrates an exemplary data flow by which the systems and methods described herein may compile a reaction history 608 that contains the actual reactions of monitored person 208 to a particular interaction or type of interaction. In this example, the systems and methods described herein may apply model 410 to sensor data 604(1)-(N) to determine prior actual reactions 606(1)-(N) of monitored person 208, respectively. In some examples, the systems and methods described herein may use reaction history 608 to train a model 404 to estimate expected reactions of the monitored person 208 to similar interactions. Additionally or alternatively, the systems and methods described herein may use reaction history 608 to derived a baseline normal reaction 610 of monitored person 208 to the same or similar interactions. In some examples, baseline normal reaction 610 may be used as or to determine an expected reaction of monitored person 208 to the same or similar interactions.

At step 306, one or more of the systems described herein may use contemporaneous sensor data to estimate the monitored person's actual reaction to the interaction. For example, sensing module 108 may, as part of computing device 202 or server 206 in FIG. 2, use sensor data 218, 220, and/or 222 to estimate actual reaction 224 of monitored person 208 to interaction 214.

The systems described herein may use contemporaneous sensor data to estimate a monitored person's actual reaction to an interaction in any suitable manner. In some examples, contemporaneous sensor data (e.g., video, images, health statistics, etc.) that was acquired or recorded when a monitored person had an interaction may include the monitored person's actual physical reactions to the interaction. In these examples, sensing module 108 may extract the monitored person's actual physical reaction from the contemporaneous sensor data. For example, sensing module 108 may identify a monitored person's microexpressions, other facial expressions, posture, tense muscles, signs of sweating, dilated pupils, glassy eyes, bruises, and/or physical signs of exhaustion from video and/or images of the monitored person that were acquired at the same time as a particular interaction. Similarly, sensing module 108 may identify auditory reactions (e.g., crying, yelling, laughing, slurred speech, etc.) from audio recordings of the monitored person that were acquired at the same time as the interaction. In other examples, sensing module 108 may identify changes in heartrate via contemporaneous sensor data acquired from a heartrate sensor at the same time as the interaction, changes in blood pressure via contemporaneous sensor data acquired from a blood pressure sensor at the same time as the interaction, changes in stress level via contemporaneous sensor data acquired from a stress-level sensor at the same time as the interaction, changes in weight via contemporaneous sensor data acquired from a smart scale at the same time as the interaction, and/or changes in skin temperature via contemporaneous sensor data acquired from a skin-temperature sensor at the same time as the interaction.

In some situations, contemporaneous sensor data that was acquired or recorded when a monitored person had an interaction may include information from which the monitored person's actual emotional reaction to the interaction may be deduced. In these examples, sensing module 108 may extract this information from the contemporaneous sensor data and use it to deduce the monitored person's actual emotional reaction to the interaction. For example, sensing module 108 may extract microexpression information from video and/or images of the monitored person and use this information to deduce the monitored person's actual emotional reaction to an interaction. Additionally or alternatively, sensing module 108 may extract physical or health statistics about a monitored person from heartrate data, blood-pressure data, stress-level data, weight data, and skin-temperature data and use this information to deduce the monitored person's actual emotional reaction to an interaction.

At step 308, one or more of the systems described herein may perform a security action based at least in part on a comparison of the monitored person's expected reaction and the monitored person's actual reaction. For example, security module 110 may, as part of computing device 202 in FIG. 2, perform security action 226 based at least in part on a comparison of expected reaction 216 and actual reaction 224.

The systems described herein may make various security determinations based on a comparison of a monitored person's expected reaction to an interaction and the monitored person's actual reaction to the interaction. Upon making a security determination, the systems described herein may perform a suitable security action (e.g., such as reporting to a child's guardian any interactions to which the child had an abnormal reaction).

In some examples, security module 110 may use a comparison of a monitored person's expected reaction to an interaction and the monitored person's actual reaction to the interaction to validate or invalidate the estimation of the expected reaction and/or the model used to make the estimation. For example, if a monitored person's expected reaction to an interaction is different than the monitored person's actual reaction to the interaction, security module 110 may determine that the monitored person's estimated expected reaction is incorrect (e.g., a false positive or a false negative) and/or that the model used to estimate the expected reaction should be updated and/or retrained to reflect the monitored person's actual reaction. In these examples, security module 110 may perform a security action based on the monitored person's actual reaction rather than the monitored person's expected reaction and/or may use the monitored person's actual reaction to update or retrain the model used to estimate the expected reaction. Alternatively, if a monitored person's expected reaction to an interaction is the same as the monitored person's actual reaction to the interaction, security module 110 may determine that the monitored person's estimated expected reaction is correct. In these examples, security module 110 may perform a security action that is commensurate with a higher confidence level.

In some examples, security module 110 may determine that a monitored person is experiencing forms of cyberbullying by determining that the monitored person's actual reactions to certain communications or people are less positive than expected. In these examples, estimating module 106 may have estimated that a communication was expected to elicit a general positive or neutral reaction, a specific positive or neutral reaction, or an unknown reaction from the monitored person. However, using contemporaneous sensor data, sensing module 108 may have determined that the communication elicited a general or specific negative reaction from the monitored person. For example, sensing module 108 may have determined that the communication elicited a specific negative reaction from the monitored person that is indicative of cyberbullying. Upon detecting instances of cyberbullying, security module 110 may report the instances to a concerned party (e.g., a child's parent or guardian).

In some examples, security module 110 may determine that a monitored person's responses to a type of interaction are abnormal by determining that the monitored person's actual reactions to the type of interaction are different (e.g., more than a predetermined number of standard deviations different) from the monitored person's expected reaction, which may be based on a normal baseline reaction to the type of interaction. By determining that a monitored person's responses to and interaction are abnormal, security module 110 may detect things such as unhealthy interest in, unusual fear of, unusual excitement with, or an obsession with a topic (e.g., addictive or dangerous substances, weapons, sports teams, statistics, celebrities, friends, etc.), a person, or an environment. In some situations, after detecting unhealthy interest, unusual excitement, or an obsession with a topic, security module 110 may prevent or limit the monitored person's access to digital content involving the topic. In this way, security module 110 may perform content filtering based on a child's actual reactions to digital content instead of just the topics of the digital content. In some examples, after detecting a monitored person's unhealthy interest, unusual excitement, or an obsession with a topic, security module 110 may report the unhealthy interest, unusual excitement, or an obsession with the topic to a parent or guardian of the monitored person.

In some examples, security module 110 may determine that a monitored person has begun experimenting with an addictive substance by determining that the monitored person's prior reactions in certain environments or situations (e.g., at home, at school, at a friend's home) differ from the person's actual reactions in these environments or situations in a way that indicates that the person has begun experimenting with the addictive substance. For example, security module 110 may compare a monitored person's previous reactions at a location with the monitored person's actual reactions at the location to determine that the monitored person is exhibiting various physical and emotional responses (e.g., dilated eyes or slurred speech) that are unexpected at the location and that may indicate that the monitored person is currently using an addictive substance. Upon completion of step 308, exemplary method 300 in FIG. 3 may terminate.

As explained above, by monitoring a child's contemporaneous physical and emotional reactions to any communications, media, people, and environments with which the child interacts, the systems and methods described herein may personalize various parental-control, child-safety, and/or cybersecurity actions and features to the child. For example, by monitoring a child's contemporaneous physical and emotional reactions to the digital communications that the child views and/or the people with which the child interacts, these systems and methods may determine, in a way that is individualized to the child, when such communications may be forms of cyberbullying and/or when such people may be bullying or otherwise harming the child. Additionally, by monitoring a child's contemporaneous physical and emotional reactions to the digital content that the child views, these systems and methods may determine when the child reacts in an abnormal way to certain types of digital content (e.g., with inappropriate excitement, interest, or obsession) and may perform suitable actions in response to this determination (e.g., preventing or limiting the child's access to these types of digital content).

Figure 7:
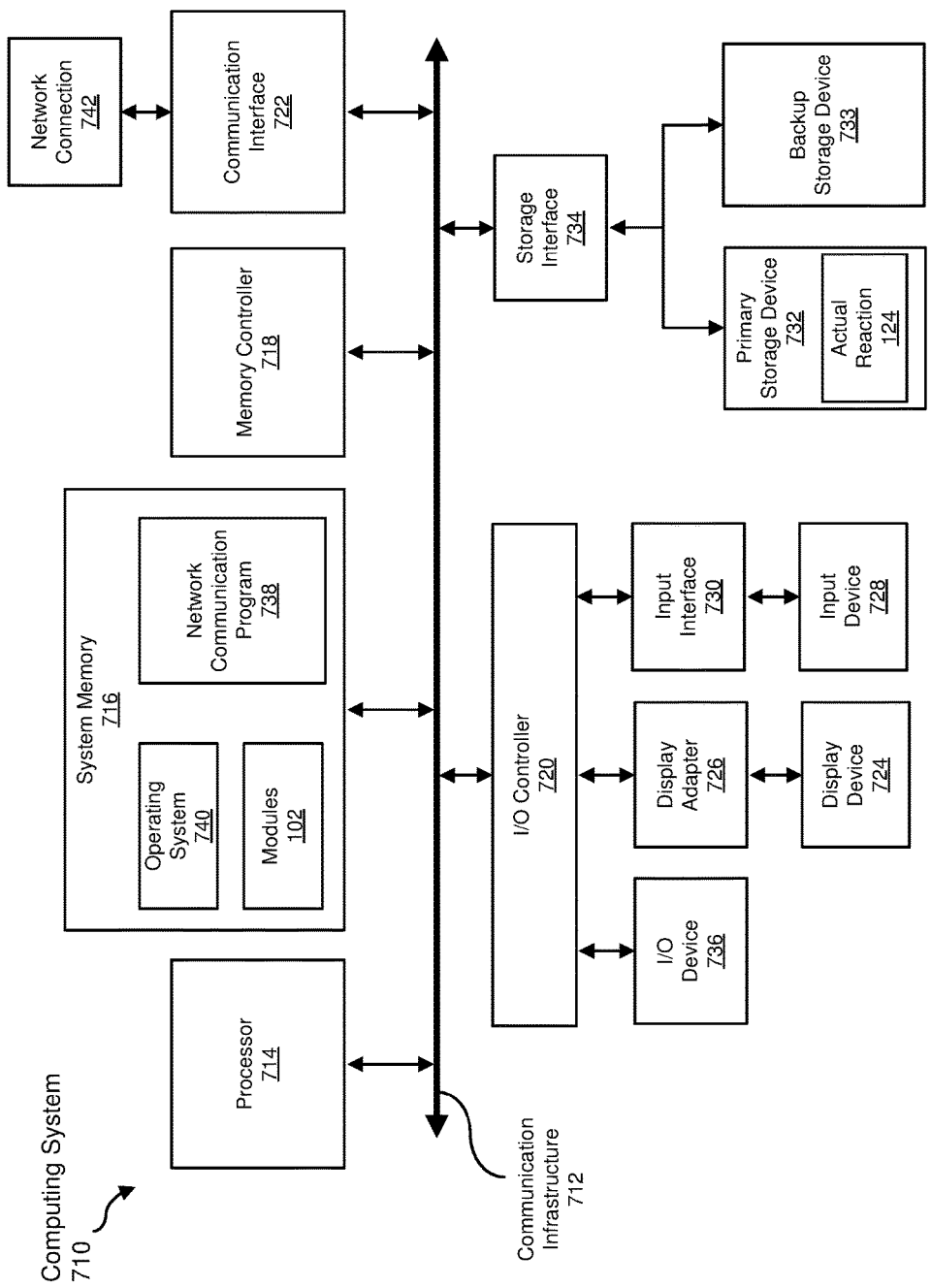
FIG. 7 is a block diagram of an example computing system capable of implementing one or more of the embodiments described and/or illustrated herein.

FIG. 7 is a block diagram of an example computing system 710 capable of implementing one or more of the embodiments described and/or illustrated herein. For example, all or a portion of computing system 710 may perform and/or be a means for performing, either alone or in combination with other elements, one or more of the steps described herein (such as one or more of the steps illustrated in FIG. 3). All or a portion of computing system 710 may also perform and/or be a means for performing any other steps, methods, or processes described and/or illustrated herein.

Computing system 710 broadly represents any single or multi-processor computing device or system capable of executing computer-readable instructions. Examples of computing system 710 include, without limitation, workstations, laptops, client-side terminals, servers, distributed computing systems, handheld devices, or any other computing system or device. In its most basic configuration, computing system 710 may include at least one processor 714 and a system memory 716.

Processor 714 generally represents any type or form of physical processing unit (e.g., a hardware-implemented central processing unit) capable of processing data or interpreting and executing instructions. In certain embodiments, processor 714 may receive instructions from a software application or module. These instructions may cause processor 714 to perform the functions of one or more of the example embodiments described and/or illustrated herein.

System memory 716 generally represents any type or form of volatile or non-volatile storage device or medium capable of storing data and/or other computer-readable instructions. Examples of system memory 716 include, without limitation, Random Access Memory (RAM), Read Only Memory (ROM), flash memory, or any other suitable memory device. Although not required, in certain embodiments computing system 710 may include both a volatile memory unit (such as, for example, system memory 716) and a non-volatile storage device (such as, for example, primary storage device 732, as described in detail below). In one example, one or more of modules 102 from FIG. 1 may be loaded into system memory 716.

In some examples, system memory 716 may store and/or load an operating system 740 for execution by processor 714. In one example, operating system 740 may include and/or represent software that manages computer hardware and software resources and/or provides common services to computer programs and/or applications on computing system 710. Examples of operating system 640 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 710 may also include one or more components or elements in addition to processor 714 and system memory 716. For example, as illustrated in FIG. 7, computing system 710 may include a memory controller 718, an Input/Output (I/O) controller 720, and a communication interface 722, each of which may be interconnected via a communication infrastructure 712. Communication infrastructure 712 generally represents any type or form of infrastructure capable of facilitating communication between one or more components of a computing device. Examples of communication infrastructure 712 include, without limitation, a communication bus (such as an Industry Standard Architecture (ISA), Peripheral Component Interconnect (PCI), PCI Express (PCIe), or similar bus) and a network.

Memory controller 718 generally represents any type or form of device capable of handling memory or data or controlling communication between one or more components of computing system 710. For example, in certain embodiments memory controller 718 may control communication between processor 714, system memory 716, and I/O controller 720 via communication infrastructure 712.

I/O controller 720 generally represents any type or form of module capable of coordinating and/or controlling the input and output functions of a computing device. For example, in certain embodiments I/O controller 720 may control or facilitate transfer of data between one or more elements of computing system 710, such as processor 714, system memory 716, communication interface 722, display adapter 726, input interface 730, and storage interface 734.

As illustrated in FIG. 7, computing system 710 may also include at least one display device 724 coupled to I/O controller 720 via a display adapter 726. Display device 724 generally represents any type or form of device capable of visually displaying information forwarded by display adapter 726. Similarly, display adapter 726 generally represents any type or form of device configured to forward graphics, text, and other data from communication infrastructure 712 (or from a frame buffer, as known in the art) for display on display device 724.

As illustrated in FIG. 7, example computing system 710 may also include at least one input device 728 coupled to I/O controller 720 via an input interface 730. Input device 728 generally represents any type or form of input device capable of providing input, either computer or human generated, to example computing system 710. Examples of input device 728 include, without limitation, a keyboard, a pointing device, a speech recognition device, variations or combinations of one or more of the same, and/or any other input device.

Additionally or alternatively, example computing system 710 may include additional I/O devices. For example, example computing system 710 may include I/O device 736. In this example, I/O device 736 may include and/or represent a user interface that facilitates human interaction with computing system 710. Examples of I/O device 736 include, without limitation, a computer mouse, a keyboard, a monitor, a printer, a modem, a camera, a scanner, a microphone, a touchscreen device, variations or combinations of one or more of the same, and/or any other I/O device.

Communication interface 722 broadly represents any type or form of communication device or adapter capable of facilitating communication between example computing system 710 and one or more additional devices. For example, in certain embodiments communication interface 722 may facilitate communication between computing system 710 and a private or public network including additional computing systems. Examples of communication interface 722 include, without limitation, a wired network interface (such as a network interface card), a wireless network interface (such as a wireless network interface card), a modem, and any other suitable interface. In at least one embodiment, communication interface 722 may provide a direct connection to a remote server via a direct link to a network, such as the Internet. Communication interface 722 may also indirectly provide such a connection through, for example, a local area network (such as an Ethernet network), a personal area network, a telephone or cable network, a cellular telephone connection, a satellite data connection, or any other suitable connection.

In certain embodiments, communication interface 722 may also represent a host adapter configured to facilitate communication between computing system 710 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 722 may also allow computing system 710 to engage in distributed or remote computing. For example, communication interface 722 may receive instructions from a remote device or send instructions to a remote device for execution.

In some examples, system memory 716 may store and/or load a network communication program 738 for execution by processor 714. In one example, network communication program 738 may include and/or represent software that enables computing system 710 to establish a network connection 742 with another computing system (not illustrated in FIG. 7) and/or communicate with the other computing system by way of communication interface 722. In this example, network communication program 738 may direct the flow of outgoing traffic that is sent to the other computing system via network connection 742. Additionally or alternatively, network communication program 738 may direct the processing of incoming traffic that is received from the other computing system via network connection 742 in connection with processor 714.

Although not illustrated in this way in FIG. 7, network communication program 738 may alternatively be stored and/or loaded in communication interface 722. For example, network communication program 738 may include and/or represent at least a portion of software and/or firmware that is executed by a processor and/or Application Specific Integrated Circuit (ASIC) incorporated in communication interface 722.

As illustrated in FIG. 7, example computing system 710 may also include a primary storage device 732 and a backup storage device 733 coupled to communication infrastructure 712 via a storage interface 734. Storage devices 732 and 733 generally represent any type or form of storage device or medium capable of storing data and/or other computer-readable instructions. For example, storage devices 732 and 733 may be a magnetic disk drive (e.g., a so-called hard drive), a solid state drive, a floppy disk drive, a magnetic tape drive, an optical disk drive, a flash drive, or the like. Storage interface 734 generally represents any type or form of interface or device for transferring data between storage devices 732 and 733 and other components of computing system 710. In one example, one or more of expected reaction 120, sensor data 122, and actual reaction 124 from FIG. 1 may be stored and/or loaded in primary storage device 732.

In certain embodiments, storage devices 732 and 733 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 732 and 733 may also include other similar structures or devices for allowing computer software, data, or other computer-readable instructions to be loaded into computing system 710. For example, storage devices 732 and 733 may be configured to read and write software, data, or other computer-readable information. Storage devices 732 and 733 may also be a part of computing system 710 or may be a separate device accessed through other interface systems.

Many other devices or subsystems may be connected to computing system 710. Conversely, all of the components and devices illustrated in FIG. 7 need not be present to practice the embodiments described and/or illustrated herein. The devices and subsystems referenced above may also be interconnected in different ways from that shown in FIG. 7. Computing system 710 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 710. All or a portion of the computer program stored on the computer-readable medium may then be stored in system memory 716 and/or various portions of storage devices 732 and 733. When executed by processor 714, a computer program loaded into computing system 710 may cause processor 714 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 710 may be configured as an Application Specific Integrated Circuit (ASIC) adapted to implement one or more of the example embodiments disclosed herein.

Figure 8:
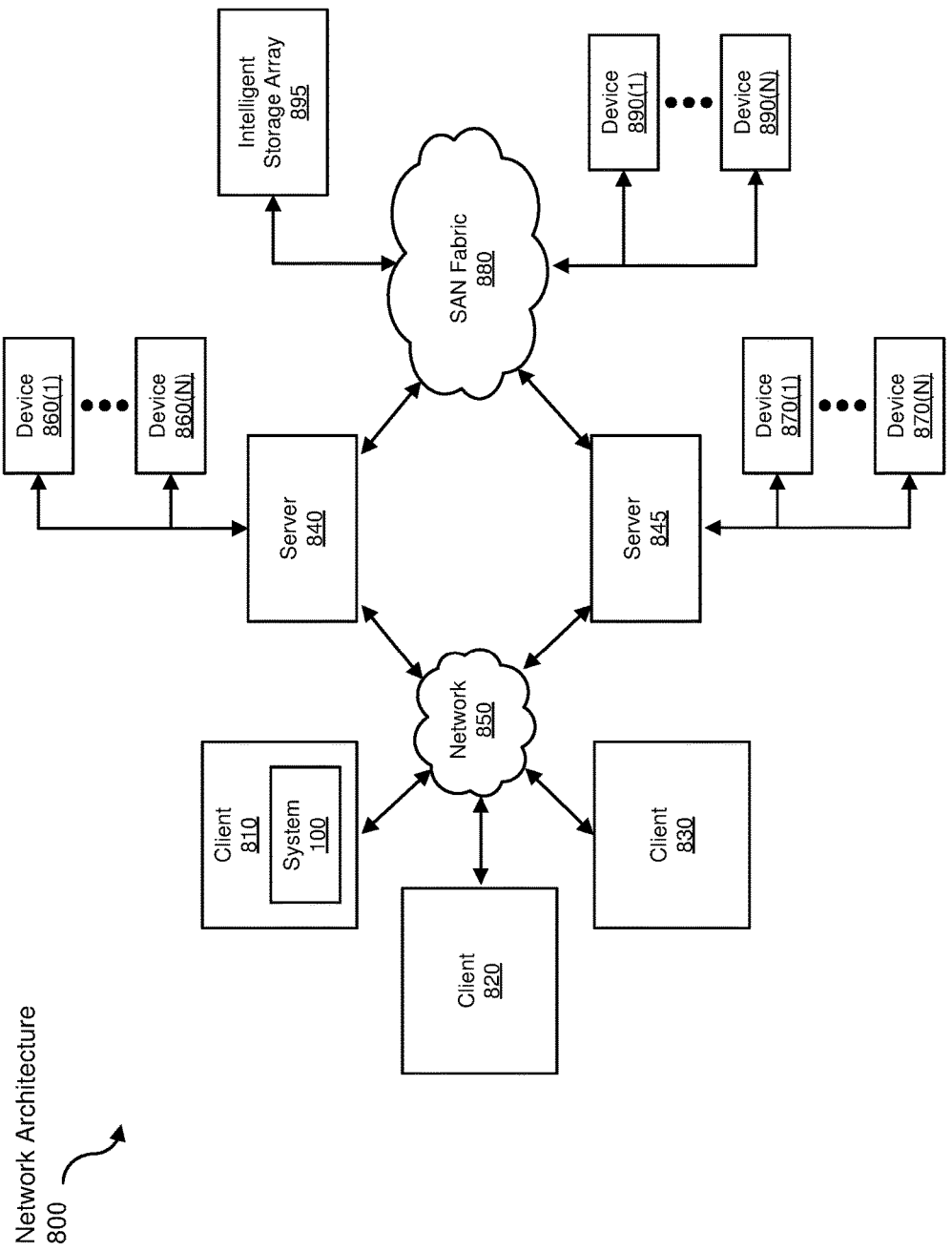
FIG. 8 is a block diagram of an example computing network capable of implementing one or more of the embodiments described and/or illustrated herein.

FIG. 8 is a block diagram of an example network architecture 800 in which client systems 810, 820, and 830 and servers 840 and 845 may be coupled to a network 850. As detailed above, all or a portion of network architecture 800 may perform and/or be a means for performing, either alone or in combination with other elements, one or more of the steps disclosed herein (such as one or more of the steps illustrated in FIG. 3). All or a portion of network architecture 800 may also be used to perform and/or be a means for performing other steps and features set forth in the instant disclosure.

Client systems 810, 820, and 830 generally represent any type or form of computing device or system, such as example computing system 710 in FIG. 7. Similarly, servers 840 and 845 generally represent computing devices or systems, such as application servers or database servers, configured to provide various database services and/or run certain software applications. Network 850 generally represents any telecommunication or computer network including, for example, an intranet, a WAN, a LAN, a PAN, or the Internet. In one example, client systems 810, 820, and/or 830 and/or servers 840 and/or 845 may include all or a portion of system 100 from FIG. 1.

As illustrated in FIG. 8, one or more storage devices 860(1)-(N) may be directly attached to server 840. Similarly, one or more storage devices 870(1)-(N) may be directly attached to server 845. Storage devices 860(1)-(N) and storage devices 870(1)-(N) generally represent any type or form of storage device or medium capable of storing data and/or other computer-readable instructions. In certain embodiments, storage devices 860(1)-(N) and storage devices 870(1)-(N) may represent Network-Attached Storage (NAS) devices configured to communicate with servers 840 and 845 using various protocols, such as Network File System (NFS), Server Message Block (SMB), or Common Internet File System (CIFS).

Servers 840 and 845 may also be connected to a Storage Area Network (SAN) fabric 880. SAN fabric 880 generally represents any type or form of computer network or architecture capable of facilitating communication between a plurality of storage devices. SAN fabric 880 may facilitate communication between servers 840 and 845 and a plurality of storage devices 890(1)-(N) and/or an intelligent storage array 895. SAN fabric 880 may also facilitate, via network 850 and servers 840 and 845, communication between client systems 810, 820, and 830 and storage devices 890(1)-(N) and/or intelligent storage array 895 in such a manner that devices 890(1)-(N) and array 895 appear as locally attached devices to client systems 810, 820, and 830. As with storage devices 860(1)-(N) and storage devices 870(1)-(N), storage devices 890(1)-(N) and intelligent storage array 895 generally represent any type or form of storage device or medium capable of storing data and/or other computer-readable instructions.

In certain embodiments, and with reference to example computing system 710 of FIG. 7, a communication interface, such as communication interface 722 in FIG. 7, may be used to provide connectivity between each client system 810, 820, and 830 and network 850. Client systems 810, 820, and 830 may be able to access information on server 840 or 845 using, for example, a web browser or other client software. Such software may allow client systems 810, 820, and 830 to access data hosted by server 840, server 845, storage devices 860(1)-(N), storage devices 870(1)-(N), storage devices 890(1)-(N), or intelligent storage array 895. Although FIG. 8 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 840, server 845, storage devices 860(1)-(N), storage devices 870(1)-(N), storage devices 890(1)-(N), intelligent storage array 895, or any combination thereof. All or a portion of one or more of the example embodiments disclosed herein may also be encoded as a computer program, stored in server 840, run by server 845, and distributed to client systems 810, 820, and 830 over network 850.

As detailed above, computing system 710 and/or one or more components of network architecture 800 may perform and/or be a means for performing, either alone or in combination with other elements, one or more steps of an example method for performing security actions based on people's actual reactions to interactions.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

According to some examples, all or a portion of example system 100 in FIG. 1 may represent portions of, communicate with, and/or receive protection from one or more systems for endpoint security. As used herein, the term "endpoint security" may refer to the protection of endpoint systems from unauthorized and/or illegitimate use, access, and/or control. Examples of systems for endpoint protection may include, without limitation, anti-malware systems, user authentication systems, encryption systems, privacy systems, spam-filtering services, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

In addition, one or more of the modules described herein may transform data, physical devices, and/or representations of physical devices from one form to another. For example, one or more of the modules recited herein may receive contemporaneous sensor data to be transformed, transform the contemporaneous sensor data into a determination of a monitored person's actual reaction to a particular interaction, output a result of the transformation to a system for comparing an expected reaction to the actual reaction, use the result of the transformation to make a security determination based on a comparison of the expected reaction to the actual reaction, and store the result of the transformation to a system for storing histories of people's actual reactions. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A computer-implemented method for performing security actions based on people's actual reactions to interactions, at least a portion of the method being performed by a computing device comprising at least one processor, the method comprising:
    detecting an interaction of a monitored person;
    estimating the monitored person's expected reaction to the interaction;
    using contemporaneous sensor data to estimate the monitored person's actual reaction to the interaction;
    comparing an estimation of the monitored person's expected reaction to an estimation of the monitored person's actual reaction; and
    performing a security action based at least in part on a comparison of the estimation of the monitored person's expected reaction and the estimation of the monitored person's actual reaction.

2. The computer-implemented method of claim 1, wherein:
    the monitored person comprises a child;
    performing the security action comprises reporting the interaction to the child's guardian.

3. The computer-implemented method of claim 1, wherein:
    detecting the interaction of the monitored person comprises detecting a communication that the monitored person views;
    estimating the monitored person's expected reaction to the interaction comprises determining that the monitored person's expected reaction to the communication should be positive;
    using the contemporaneous sensor data to estimate the monitored person's actual reaction to the interaction comprises using the contemporaneous sensor data to determine that the monitored person's actual reaction to the communication was negative; and
    comparing the estimation of the monitored person's expected reaction to the estimation of the monitored person's actual reaction comprises identifying a difference between the estimation of the monitored person's expected reaction and the estimation of the monitored person's actual reaction;
    performing the security action comprises determining, based at least in part on the difference, that the communication is a form of cyberbullying.

4. The computer-implemented method of claim 1, wherein:
    estimating the monitored person's expected reaction to the interaction comprises:
        using additional sensor data to estimate at least one additional monitored person's actual reaction to a similar interaction; and
        using the at least one additional monitored person's actual reaction to the similar interaction to establish a baseline normal reaction to the interaction; and
    the monitored person's expected reaction to the interaction is based at least in part on the baseline normal reaction to the interaction.

5. The computer-implemented method of claim 4, wherein:
    comparing the estimation of the monitored person's expected reaction to the estimation of the monitored person's actual reaction comprises identifying a difference between the estimation of the monitored person's actual reaction and the baseline normal reaction;
    performing the security action comprises determining, based at least in part on the difference, that the monitored person's actual reaction to the interaction is abnormal.

6. The computer-implemented method of claim 1, wherein:
    estimating the monitored person's expected reaction to the interaction comprises using prior sensor data to estimate a prior reaction of the monitored person to a similar interaction; and
    the monitored person's expected reaction to the interaction is based at least in part on the prior reaction of the monitored person to the similar interaction.

7. The computer-implemented method of claim 6, wherein:
    comparing the estimation of the monitored person's expected reaction to the estimation of the monitored person's actual reaction comprises identifying a difference between the estimation of the monitored person's expected reaction and the estimation of the monitored person's actual reaction;
    performing the security action comprises determining, based at least in part on the difference, that the monitored person's actual reaction to the interaction is abnormal.

8. The computer-implemented method of claim 1, wherein using the contemporaneous sensor data to estimate the monitored person's actual reaction to the interaction comprises:
    using contemporaneous camera data to detect a microexpression that was exhibited by the monitored person as the monitored person had the interaction; and
    deriving the monitored person's actual reaction to the interaction based at least in part on the microexpression that was exhibited by the monitored person.

9. The computer-implemented method of claim 1, wherein:
    the contemporaneous sensor data indicates an actual physical reaction of the monitored person to the interaction; and
    using the contemporaneous sensor data to estimate the monitored person's actual reaction to the interaction comprises estimating the monitored person's actual emotional reaction to the interaction based at least in part on the actual physical reaction of the monitored person to the interaction.

10. The computer-implemented method of claim 9, wherein the contemporaneous sensor data indicates at least one of:
    the monitored person's heartrate at the time of the interaction;
    the monitored person's blood pressure at the time of the interaction;

the monitored person's stress level at the time of the interaction; and the monitored person's skin temperature at the time of the interaction.

11. The computer-implemented method of claim 1, wherein:

detecting the interaction of the monitored person comprises detecting digital content with which the monitored person interacts;

estimating the monitored person's expected reaction to the interaction comprises estimating the monitored person's expected reaction to the digital content; and using the contemporaneous sensor data to estimate the monitored person's actual reaction to the interaction comprises using the contemporaneous sensor data to estimate the monitored person's actual reaction to the digital content.

12. The computer-implemented method of claim 1, wherein:

detecting the interaction of the monitored person comprises detecting an additional person with which the monitored person interacts;

estimating the monitored person's expected reaction to the interaction comprises estimating the monitored person's expected reaction to the additional person; and using the contemporaneous sensor data to estimate the monitored person's actual reaction to the interaction comprises using the contemporaneous sensor data to estimate the monitored person's actual reaction to the additional person.

13. The computer-implemented method of claim 1, wherein:

detecting the interaction of the monitored person comprises detecting an environment with which the monitored person interacts;

estimating the monitored person's expected reaction to the interaction comprises estimating the monitored person's expected reaction to the environment; and using the contemporaneous sensor data to estimate the monitored person's actual reaction to the interaction comprises using the contemporaneous sensor data to estimate the monitored person's actual reaction to the environment.

14. The computer-implemented method of claim 1, wherein:

estimating the monitored person's expected reaction to the interaction comprises using information about the interaction as input to a first model that outputs the estimation of the monitored person's expected reaction;

using contemporaneous sensor data to estimate the monitored person's actual reaction to the interaction comprises using the contemporaneous sensor data as input to a second model that outputs the estimation of the monitored person's actual reaction.

15. A system for performing security actions based on people's actual reactions to interactions, the system comprising:

a detecting module, stored in memory, that detects an interaction of a monitored person;

an estimating module, stored in memory, that estimates the monitored person's expected reaction to the interaction;

a sensing module, stored in memory, that uses contemporaneous sensor data to estimate the monitored person's actual reaction to the interaction;

a security module, stored in memory, that:

compares an estimation of the monitored person's expected reaction to an estimation of the monitored person's actual reaction; and performs a security action based at least in part on a comparison of the estimation of the monitored person's expected reaction and the estimation of the monitored person's actual reaction; and at least one physical processor that executes the detecting module, the estimating module, the sensing module, and the security module.

16. The system of claim 15, wherein:

the monitored person comprises a child;

the security module performs the security action by reporting the interaction to the child's guardian.

17. The system of claim 15, wherein:

the detecting module detects the interaction of the monitored person by detecting a communication that the monitored person views;

the estimating module estimates the monitored person's expected reaction to the interaction by determining that the monitored person's expected reaction to the communication should be positive;

the sensing module uses the contemporaneous sensor data to estimate the monitored person's actual reaction to the interaction by using the contemporaneous sensor data to determine that the monitored person's actual reaction to the communication was negative; and the security module performs the security action by:

comparing the estimation of the monitored person's expected reaction to the estimation of the monitored person's actual reaction comprises identifying a difference between the estimation of the monitored person's expected reaction and the estimation of the monitored person's actual reaction; and determining, based at least in part on the difference, that the communication is a form of cyberbullying.

18. The system of claim 15, wherein:

the estimating module estimates the monitored person's expected reaction to the interaction by:

using additional sensor data to estimate at least one additional monitored person's actual reaction to a similar interaction; and using the at least one additional monitored person's actual reaction to the similar interaction to establish a baseline normal reaction to the interaction; and the monitored person's expected reaction to the interaction is based at least in part on the baseline normal reaction to the interaction.

19. The system of claim 18, wherein the security module performs the security action by:

comparing the estimation of the monitored person's expected reaction to the estimation of the monitored person's actual reaction comprises identifying a difference between the estimation of the monitored person's actual reaction and the baseline normal reaction;

determining, based at least in part on the difference, that the monitored person's actual reaction to the interaction is abnormal.

20. A non-transitory computer-readable medium comprising one or more computer-executable instructions that, when executed by at least one processor of a computing device, cause the computing device to:

detect an interaction of a monitored person;

estimate the monitored person's expected reaction to the interaction;

use contemporaneous sensor data to estimate the monitored person's actual reaction to the interaction;

compare an estimation of the monitored person's expected reaction to an estimation of the monitored person's actual reaction; and perform a security action based at least in part on a comparison of the estimation of the monitored person's expected reaction and the estimation of the monitored person's actual reaction.

\* \* \* \* \*